United States Patent
Doughty

(10) Patent No.: US 10,244,878 B2
(45) Date of Patent: Apr. 2, 2019

(54) SLEEPING SUPPORT ASSEMBLY

(71) Applicant: Timothy Doughty, Bloomfield, IN (US)

(72) Inventor: Timothy Doughty, Bloomfield, IN (US)

( * ) Notice: Subject to any disclaimer, the term of this patent is extended or adjusted under 35 U.S.C. 154(b) by 0 days.

(21) Appl. No.: 15/426,622

(22) Filed: Feb. 7, 2017

(65) Prior Publication Data
US 2018/0220818 A1  Aug. 9, 2018

(51) Int. Cl.
A47G 9/10 (2006.01)
A61F 5/56 (2006.01)

(52) U.S. Cl.
CPC ......... A47G 9/1054 (2013.01); A47G 9/1072 (2013.01); A61F 5/56 (2013.01); A47G 2009/1018 (2013.01)

(58) Field of Classification Search
CPC ...... A47G 9/10; A47G 9/1054; A47G 9/1063; A47G 9/1072; A47G 9/109; A47G 9/1022; A47G 2009/1018; A61F 5/56; A47C 17/70; A47C 17/82; A47C 20/025; A47C 20/026; A47C 20/027; A47C 20/04; A47D 13/083; A47D 15/003; A47D 15/005; A47D 15/008
See application file for complete search history.

(56) References Cited

U.S. PATENT DOCUMENTS

| 4,394,783 | A | * | 7/1983 | Simmons | A47C 7/425 297/230.1 |
| 4,970,742 | A | * | 11/1990 | Keener | A47C 20/027 5/633 |
| 4,987,625 | A | * | 1/1991 | Edelson | A47C 20/026 5/420 |
| 5,632,050 | A | * | 5/1997 | Zajas | A47C 20/026 5/632 |
| 5,893,183 | A | | 4/1999 | Bechtold, Jr. | |
| 6,154,903 | A | | 12/2000 | Wai-Chung | |
| 6,185,768 | B1 | | 2/2001 | Schlechter | |
| 6,823,545 | B1 | * | 11/2004 | Davis | A47C 16/02 5/630 |
| 7,020,918 | B1 | * | 4/2006 | Tinsley | A47C 16/00 5/630 |
| 7,661,163 | B1 | * | 2/2010 | Gallaher | A47C 20/021 5/632 |
| 8,056,166 | B2 | | 11/2011 | Calvart | |
| D686,027 | S | * | 7/2013 | Wagner | D6/601 |
| 9,943,179 | B1 | * | 4/2018 | May | A47C 7/383 |
| 2004/0226096 | A1 | * | 11/2004 | Davis | A47C 16/02 5/632 |

(Continued)

FOREIGN PATENT DOCUMENTS

| WO | WO9705807 | 2/1997 | |
| WO | WO-2018112277 A1 | * 6/2018 | ............ A47C 7/383 |

Primary Examiner — Robert G Santos

(57) ABSTRACT

A sleeping support assembly for reposing in a prone position includes a first cushion that is configured to support a torso of a user. A second cushion is coupled to and extends from a first end of the first cushion. A penetration is positioned through the second cushion. The penetration is substantially ovally shaped. The penetration is configured to support a head of the user who is pronely positioned upon the first cushion such that a spine of the user is aligned. The arms of the user are positioned such that blood flow to the arms is unimpaired.

9 Claims, 3 Drawing Sheets

(56) References Cited

U.S. PATENT DOCUMENTS

| | | | |
|---|---|---|---|
| 2013/0245395 A1* | 9/2013 | Bidarian Moniri | A47C 20/026 600/301 |
| 2016/0081485 A1* | 3/2016 | Tovar | A47C 20/025 5/631 |
| 2016/0278535 A1* | 9/2016 | Koutsouradis | A47C 20/026 |
| 2018/0220818 A1* | 8/2018 | Doughty | A47G 9/1054 |
| 2018/0228306 A1* | 8/2018 | May | A47C 7/38 |

* cited by examiner

SLEEPING SUPPORT ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to sleeping support assemblies and more particularly pertains to a new sleeping support assembly for reposing in a prone position.

BRIEF SUMMARY OF THE INVENTION

An embodiment of the disclosure meets the needs presented above by generally comprising a first cushion that is configured to support a torso of a user. A second cushion is coupled to and extends from a first end of the first cushion. A penetration is positioned through the second cushion. The penetration is substantially ovally shaped. The penetration is configured to support a head of the user who is pronely positioned upon the first cushion such that a spine of the user is aligned. The arms of the user are positioned such that blood flow to the arms is unimpaired.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
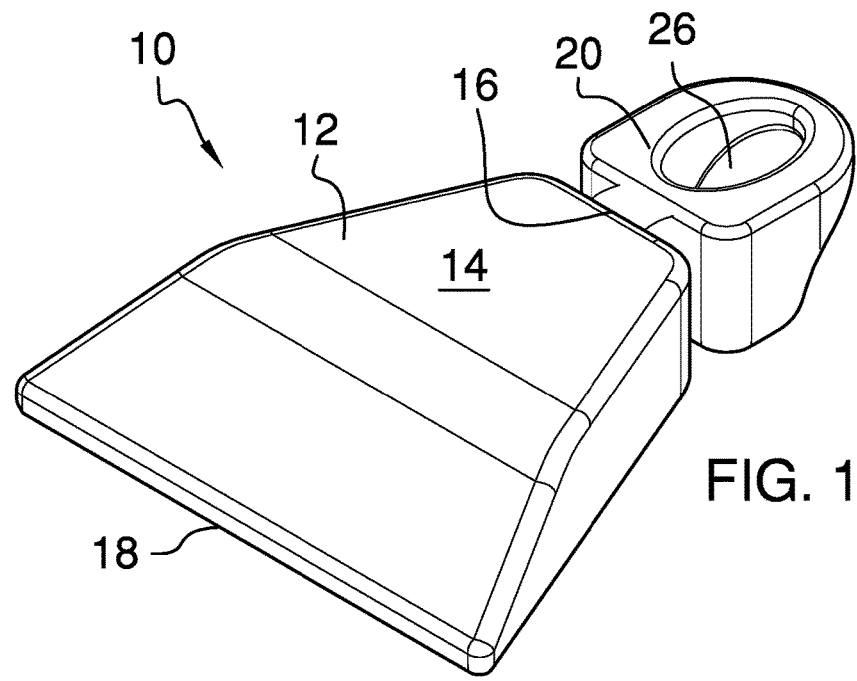
FIG. 1 is an isometric perspective view of a sleeping support assembly according to an embodiment of the disclosure.
Figure 2:
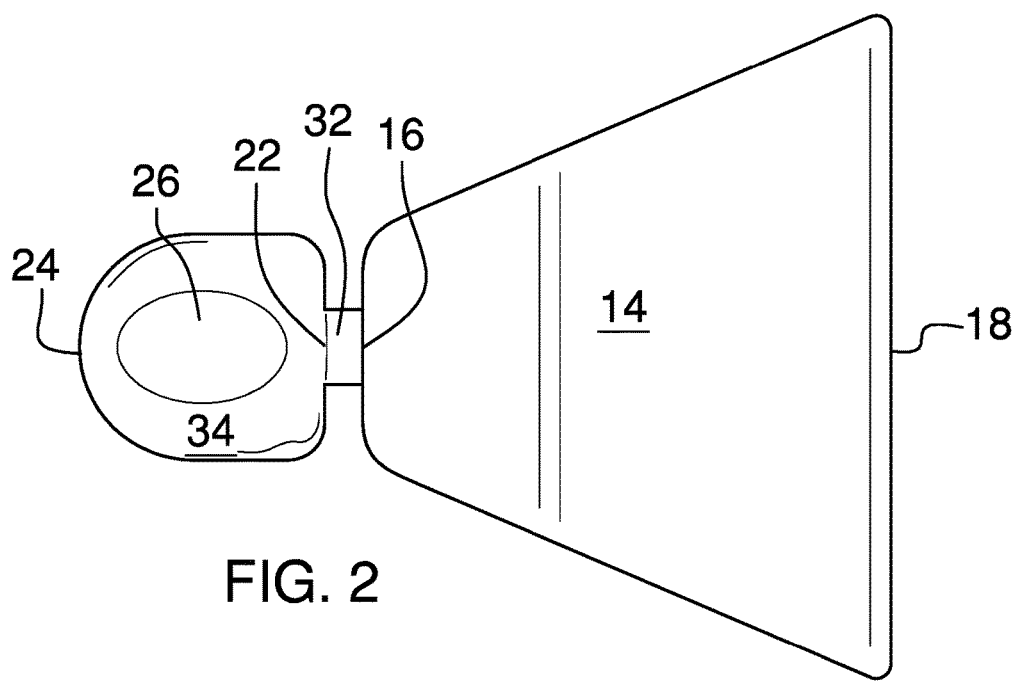
FIG. 2 is a top view of an embodiment of the disclosure.
Figure 3:
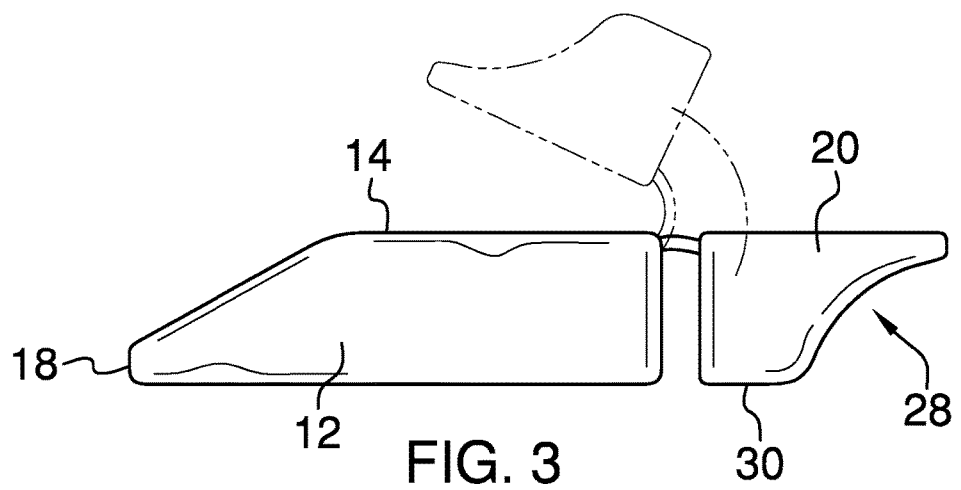
FIG. 3 is a side view of an embodiment of the disclosure.
Figure 4:
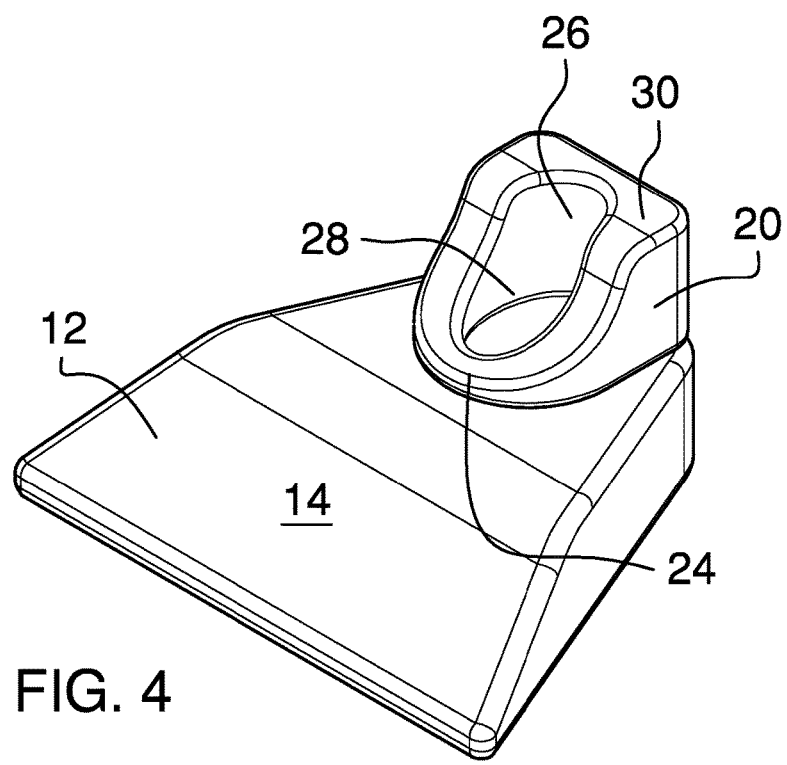
FIG. 4 is an isometric perspective view of an embodiment of the disclosure.
Figure 5:
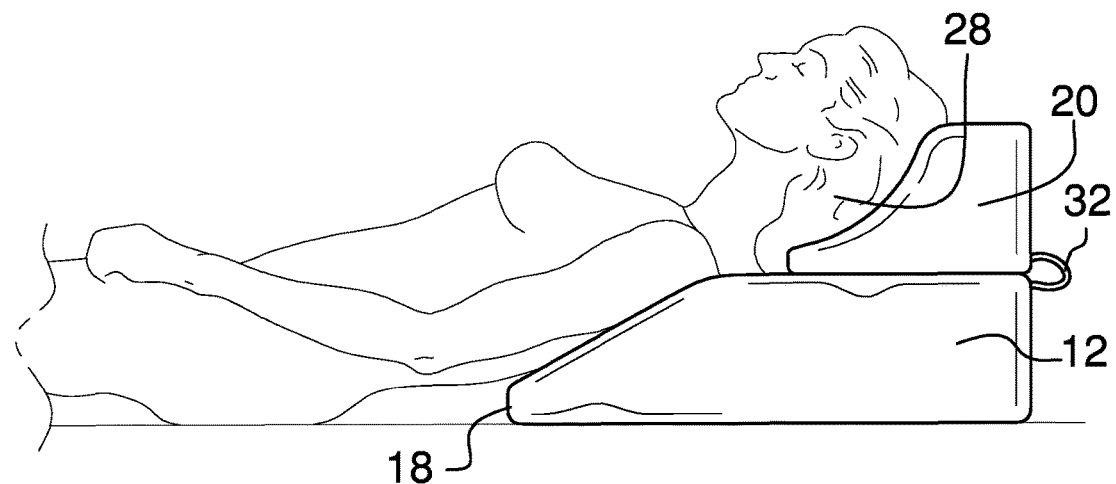
FIG. 5 is an in-use view of an embodiment of the disclosure.
Figure 6:
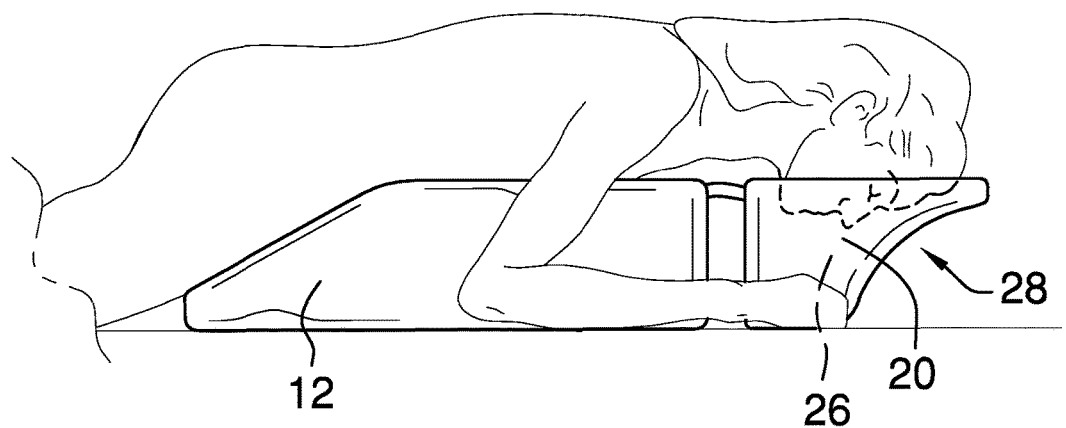
FIG. 6 is an in-use view of an embodiment of the disclosure.

With reference now to the drawings, and in particular to FIGS. 1 through 6 thereof, a new sleeping support assembly embodying the principles and concepts of an embodiment of the disclosure and generally designated by the reference numeral 10 will be described.

As best illustrated in FIGS. 1 through 6, the sleeping support assembly 10 generally comprises a first cushion 12 that is configured to support a torso of a user. The first cushion 12 has a top 14. In one embodiment, the first cushion 12 is truncated triangularly shaped when viewed from the top 14, such that a first end 16 of the first cushion 12 is dimensionally narrower than a second end 18. The first cushion 12 is cuneal adjacent to the second end 18. The first cushion 12 is configured to position beneath the torso of the user with the second end 18 positioned proximate to a pelvis of the user and the first end 16 positioned proximate to a collar bone of the user. In yet another embodiment, the first cushion 12 comprises foam. In still yet another embodiment, the first cushion 12 comprises viscoelastic polyurethane foam.

A second cushion 20 is coupled to and extends from the first end 16 of the first cushion 12. The second cushion 20 has a first endpoint 22 and a second endpoint 24. The first endpoint 22 is positioned proximate to the first end 16 of the first cushion 12. The second endpoint 24 is positioned distal from the first cushion 12. In one embodiment, the second endpoint 24 is arcuate. In another embodiment, the second cushion 20 comprises foam. In yet another embodiment, the second cushion 20 comprises viscoelastic polyurethane foam.

A penetration 26 is positioned through the second cushion 20. The penetration 26 is substantially ovally shaped. The penetration 26 is configured to support a head of the user who is pronely positioned upon the first cushion 12, such that a spine of the user is aligned. The arms of the user are positioned such that blood flow to the arms is unimpaired.

A cutout 28 is positioned in a first face 30 of the second cushion 20. The cutout 28 is fluidically coupled to the penetration 26. The cutout 28 is configured to allow airflow to the head of the user. In one embodiment, the cutout 28 is arcuate.

A strap 32 is coupled to and extends between the first end 16 of the first cushion 12 and the first endpoint 22 of the second cushion 20. The strap 32 is positioned proximate to the top 14 of the first cushion 12 and a second face 34 of the second cushion 20. The strap 32 is positioned to allow positioning of the second face 34 of the second cushion 20 upon the top 14 of the first cushion 12. The cutout 28 is configured to support the head of the user who is positioned semi-supinely upon the first cushion 12. The first cushion 12 and the second cushion 20 are configured to alleviate snoring and sleep apnea of the user.

In use, the penetration 26 is configured to support the head of the user who is pronely positioned upon the first cushion 12. The spine of the user is aligned and the arms of the user are positioned so that the blood flow to the arms is unimpaired. The second cutout 28 is configured to allowing airflow to the head of the user. The strap 32 is positioned to allow positioning of the second face 34 of the second cushion 20 upon the top 14 of the first cushion 12. The cutout 28 is configured to support the head of the user who is positioned semi-supinely upon the first cushion 12. The first cushion 12 and the second cushion 20 are configured to alleviate the snoring and the sleep apnea of the user.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A sleeping support assembly comprising:
   a first cushion configured for supporting a torso of a user, said first cushion having a first end and a second end;
   a second cushion coupled to and extending from said first end of said first cushion, said second cushion having a first endpoint and a second endpoint, said first endpoint being positioned proximate to said first end of said first cushion, said second cushion having a first face and a second face;
   a penetration positioned and extending fully through said second cushion, said penetration being substantially oval shaped;
   wherein said penetration is positioned through said second cushion such that said penetration is configured for supporting a head of the user who is pronely positioned upon said first cushion such that a spine of the user is aligned and wherein arms of the user are positioned such that blood flow to the arms is unimpaired;
   a cutout positioned in said first face of said second cushion, said cutout being fluidically coupled to said penetration, wherein said cutout is positioned in said second cushion such that said cutout is configured for allowing airflow to the head of the user, said cutout defining an arcuate surface such that said arcuate surface is increasing in slope extending away from said second end of said first cushion when said second face is positioned on a top of said first cushion; and a strap coupled to and extending between said first end of said first cushion and said first endpoint of said second cushion, said strap being positioned proximate to said top of said first cushion and said second face of said second cushion, wherein said strap is positioned on said first cushion such that said strap is positioned for positioning said second face of said second cushion upon said top of said first cushion such that said cutout is configured for supporting the head of the user who is positioned semi-supinely upon said first cushion.

2. The assembly of claim 1, further wherein said first cushion being truncated triangularly shaped when viewed from said top of said first cushion such that said first end of said first cushion is dimensionally narrower than said second end.

3. The assembly of claim 2, further including said first cushion being cuneal adjacent to said second end, wherein said first cushion is configured for positioning beneath the torso of the user with said second end positioned proximate to a pelvis of the user and said first end positioned proximate to a collar bone of the user.

4. The assembly of claim 1, further including said first cushion comprising foam.

5. The assembly of claim 4, further including said first cushion comprising viscoelastic polyurethane foam.

6. The assembly of claim 1, further including said second endpoint being arcuate.

7. The assembly of claim 1, further including said second cushion comprising foam.

8. The assembly of claim 7, further including said second cushion comprising viscoelastic polyurethane foam.

9. A sleeping support assembly comprising:
   a first cushion configured for supporting a torso of a user, said first cushion having a top, said first cushion being truncated triangularly shaped when viewed from said top such that a first end of said first cushion is dimensionally narrower than a second end, said first cushion being cuneal adjacent to said second end, wherein said first cushion is configured for positioning beneath the torso of the user with said second end positioned proximate to a pelvis of the user and said first end positioned proximate to a collar bone of the user, said first cushion comprising viscoelastic polyurethane foam;
   a second cushion coupled to and extending from said first end of said first cushion, said second cushion having a first endpoint and a second endpoint, said first endpoint being positioned proximate to said first end of said first cushion, said second endpoint being positioned distal from said first cushion, said second endpoint being arcuate, said second cushion comprising viscoelastic polyurethane foam;
   a penetration positioned through said second cushion, said penetration being substantially oval shaped, wherein said penetration is positioned through said second cushion such that said penetration is configured for supporting a head of the user who is pronely positioned upon said first cushion such that a spine of the user is aligned and wherein arms of the user are positioned such that blood flow to the arms is unimpaired;
   a cutout positioned in a first face of said second cushion, said cutout being fluidically coupled to said penetration, wherein said cutout is positioned in said second cushion such that said cutout is configured for allowing airflow to the head of the user;

a strap coupled to and extending between said first end of said first cushion and said first endpoint of said second cushion, said strap being positioned proximate to said top of said first cushion and a second face of said second cushion, wherein said strap is positioned on said first cushion such that said strap is positioned for positioning said second face of said second cushion upon said top of said first cushion such that said cutout is configured for supporting the head of the user who is positioned semi-supinely upon said first cushion, such that said first cushion and said second cushion are configured for alleviating snoring and sleep apnea of the user; and wherein said cutout defines an arcuate surface such that said arcuate surface is increasing in slope extending away from said second end of said first cushion when said second face is positioned on said top of said first cushion.

\* \* \* \* \*